United States Patent [19]
Melsky et al.

[11] Patent Number: 5,704,915
[45] Date of Patent: Jan. 6, 1998

[54] HEMODIALYSIS ACCESS DEVICE

[75] Inventors: Gerald S. Melsky, Lexington; Frank R. Prosl, Duxbury, both of Mass.

[73] Assignee: Therex Limited Partnership, Walpole, Mass.

[21] Appl. No.: 388,530

[22] Filed: Feb. 14, 1995

[51] Int. Cl.⁶ .................................................. A61M 5/00
[52] U.S. Cl. ................................... 604/175; 604/284
[58] Field of Search ........................... 604/93, 164, 175, 604/280, 283, 284

[56]      References Cited

U.S. PATENT DOCUMENTS

| | | | |
|---|---|---|---|
| 4,385,631 | 5/1983 | Uthmann | 604/284 |
| 4,496,350 | 1/1985 | Cosentino | 604/175 |
| 4,673,394 | 6/1987 | Fenton, Jr. et al. | 604/175 |
| 4,692,146 | 9/1987 | Hilger . | |
| 4,711,251 | 12/1987 | Stokes . | |
| 4,781,695 | 11/1988 | Dalton | 604/175 |
| 4,892,518 | 1/1990 | Cupp et al. . | |
| 4,915,690 | 4/1990 | Cone et al. | 604/175 X |
| 4,929,236 | 5/1990 | Sampson . | |
| 4,973,313 | 11/1990 | Katsaros et al. . | |
| 5,041,098 | 8/1991 | Loiterman et al. . | |
| 5,084,015 | 1/1992 | Moriuchi . | |
| 5,092,849 | 3/1992 | Sampson | 604/175 |
| 5,112,303 | 5/1992 | Pudenz et al. . | |
| 5,147,483 | 9/1992 | Melsky et al. . | |
| 5,167,638 | 12/1992 | Felix et al. | 604/283 X |
| 5,269,772 | 12/1993 | Wilk | 604/284 |
| 5,360,407 | 11/1994 | Leonard | 604/175 |

FOREIGN PATENT DOCUMENTS

| | | |
|---|---|---|
| 0 309 092 | 3/1989 | European Pat. Off. . |
| 2 658 082 | 8/1991 | France . |
| 36 18 390 | 11/1987 | Germany . |
| 94/05246 | 9/1993 | WIPO . |

*Primary Examiner*—Sam Rimell
*Attorney, Agent, or Firm*—Amster, Rothstein & Ebenstein

[57]      ABSTRACT

A vascular access device for hemodialysis comprises a pair of similar, generally conical, hollow shells, each shell having a relatively large entrance end and a relatively small exit end and an axis extending between the ends, the shells being connected together along a line of tangency. A pair of self-sealing septa close the entrance ends of the shells, and a pair of integral outlet tubes extend from the exit ends of the pair of shells, the distal ends of the outlet tubes being spaced apart and disposed parallel to the line of tangency.

19 Claims, 1 Drawing Sheet

HEMODIALYSIS ACCESS DEVICE

FIELD OF THE INVENTION

This invention relates to implantable vascular access devices. It relates more particularly to a vascular access device particularly suitable for hemodialysis.

BACKGROUND OF THE INVENTION

Hemodialysis is standard therapy for the treatment of end-stage renal disease. The treatment involves connecting the patient to a dialysis or kidney machine which cleanses the patient's blood of waste products such as urea and water. Typically, the treatment is carried out three times per week.

One of the major difficulties with chronic hemodialysis is the establishment and maintenance of access to the patient's vascular system for the purpose of withdrawing the blood to be dialyzed and returning the dialyzed blood to the patient. The preferred method for chronic hemodialysis access is the creation of an arterio-venous fistula in the arm of the patient. The fistula is a surgical connection of an artery to a vein. When such a connection is created, the blood flow through the blood vessels involved is increased since the flow resistant capillaries are bypassed. The pressure at the venous side of the fistula is also increased, causing the vein to enlarge its diameter and causing the walls of the vein to thicken. Once these changes have taken place, the transformed vein becomes a site with a suitably large diameter and blood flow, e.g., 150 ml/min., to puncture with needles for the purpose of connecting the patient to a dialysis machine.

However, it is often the case that the anatomy of the patient's blood vessels is not suitable for the formation of a fistula or that the patient's blood vessels are not healthy enough for a fistula to be created. In these patients, it is common practice to use an artificial vessel, called a vascular graft, to make the connection between the artery and the vein. The material of the graft is suitable for puncturing with needles to achieve the necessary access to the patient's blood system.

These prior types of vascular access are not without problems. For example, the above described fistulas and grafts frequently become partially or wholly occluded by thrombus or blood clots. Such occlusions limit the blood flow rate which can be induced during dialysis, thereby reducing the effectiveness of that procedure. Dialysis access is also complicated if the graft or fistula becomes infected. When such problems occur, surgical intervention is often necessary in order to restore the venous access to a useful condition. In many cases, however, the access is not salvageable and a completely new access must be created. In this connection, we should point out that when a graft or a fistula is created initially or salvaged, it cannot be used immediately after the surgery. A period of 6 to 8 weeks must elapse during which time the access is allowed to mature. Meanwhile, the patient must still be dialyzed.

In situations where a graft or fistula is unavailable because of the access being new or newly revised, or after having encountered a problem with an existing access, an external catheter is used to provide temporary access to the patient's venous system. For patients with diseased vasculature, or in the case of those who cannot tolerate the surgery necessary to create a graft or fistula, an external catheter is used as the principle hemodialysis access. These catheters consist of a tube, generally made of silicon rubber, having a round or oval crossection and two lumens. One end of the tube, referred to as the distal end, resides in the patient's vasculature. A common location for that end is in the superior vena cava, but the femoral vein is also used. The other, proximal end of the catheter lies outside the patient's skin so that it is accessible by medical personnel performing the dialysis. That end is usually fitted with Luer connectors for coupling the dual lumen catheter to conduits leading to the dialysis machine.

The connectors at the proximal end of the catheter, while offering a "needle free" means of connecting the patient to the dialysis machine, are very difficult to maintain in a sterile condition. Once these connectors become contaminated, the organisms are transmitted to the patient during dialysis. Also, even though these catheters are flushed with heparinized solutions after each use, their lumens frequently become occluded with thrombus. This is due, in part, to blood being drawn into the lumens in order to make up for the volume of fluid lost by the process of diffusion through the wall of that segment of the catheter which resides outside of the patient.

To avoid the problem of infection, it has been proposed to provide an implantable vascular access port at the proximal end of the catheter so that the connections of the dialysis machine to the patient can be made subcutaneously. Such ports have long been used to provide vascular access for chemotherapy. However, the design of those devices does not allow them to be used for hemodialysis because their flow resistance is too high to permit the blood flow rates required in dialysis.

Among the masons for this am the needle sizes used to access conventional ports are kept small in order to prevent excessive damage to the resealable silicon rubber septa in the portal; the fluid flow through the port is required to make abrupt turns, creating turbulence in the blood flow, and the blood flow path through an access needle and into the patient contains abrupt enlargements and restrictions which also encourage turbulent flow. Such turbulence not only reduces the blood flow rate, but also promotes the formation of thrombus.

SUMMARY OF THE INVENTION

The present invention aims to provide an alternative means of hemodialysis which overcomes the problems of infection and lumen occlusion associated with external hemodialysis access catheters.

Another object of the invention is to provide a vascular access device having a relatively low flow resistance for permitting the blood flow rates required in dialysis.

Another object of the invention is to provide such a vascular access device which minimizes turbulence associated with blood flow through the device.

Still another object of the invention is to provide a vascular access device which is relatively safe to use.

A further object is to provide a vascular access device whose septa are not prone to leakage even over the long term.

Yet another object of the invention is to provide a device of this type which minimizes thrombus formation and damage to the blood cells.

Still another object of the invention is to provide a vascular access device which is relatively easy to manufacture in quantity.

A further object of the invention is to provide a vascular access device which can remain in a patient for a prolonged period without undo discomfort to the patient.

Other objects will, in part, be obvious and will, in part, appear hereinafter. The invention accordingly comprises the features of construction, combination of elements and arrangement of parts which will be exemplified in the following detailed description and the scope of the invention will be indicated in the claims.

Our vascular access device comprises a dual-access port head connected to a dual lumen flexible catheter, the entire device being totally implantable. Each port head includes a septum which may be penetrated easily by a hypodermic needle which acts as a conduit for injecting or aspirating fluid through the device. When the needle is withdrawn, the septum re-seals due to compressive stresses in the septum material created at the time of manufacture. Because of its shape and relatively large area, each septum may be made as a bi-durometer device in other words, it may consist of two different durometer rubbers. The outer layer or portion of the septum may be a relatively hard durometer rubber which prevents the septum from ballooning under pressure and gives the septum overall structural integrity. The inner layer of the septum may be of a much softer rubber which has excellent resealing characteristics. Resultantly, the septum will be able to withstand numerous needle punctures without leakage.

As we shall see, especially large needles, i.e., 16 gage or less, to be described in detail later, are provided for accessing the device. Each needle has a stylet which occludes the lumen of the needle during insertion through the device's septum. With the stylet in place, the needle cannula can penetrate the septum without coring the septum material. Once the needle is in place, the stylet is removed and the hub of the needle may be connected to an infusion line leading to the dialysis machine.

The dual-access port head comprises a pair of conical shells joined at their outer surfaces along a line of tangency. The large opening into each shell is closed by a needle-penetrable self-sealing septum. An outlet tube is connected to the small opening of each shell, those tubes being bent so that they curve away from the conical axes of the respective shells and lie parallel to one another, being spaced apart a distance equal to the spacing of the two lumens of the catheter connected to the head. This head construction places the septum of each shell directly opposite the outlet tube for that shell so that when a needle accesses one of the shells, it will lie, more or less, in line with the outlet tube for that shell. Resultantly, blood from that needle will flow in a substantially direct path to the outlet tube thereby minimizing turbulence. Also, the conical shape of each shell of the head provides for the gradual contraction of the fluid flow from the needle to the outlet tube, further minimizing flow resistance and blood-damaging turbulence associated with flow through fluid passages which have abrupt changes in direction and diameter.

The slight bends in the shells' outlet tubes provide an additional safety feature in that they prevent the access needles from being advanced entirely through the outlet tubes to a degree where the tips of the needles can puncture the walls of the attached catheter.

Conical port shells having the above features may be manufactured easily by machining a radially symmetric conical body with a straight outlet tube whose axis is coincident with the axis of the conical shell and then bending the outlet tube to the requisite degree. Therefore, the cost of the access device can be kept to a minimum.

BRIEF DESCRIPTION OF THE DRAWING

For a fuller understanding of the nature and objects of the invention, reference should be had to the following detailed description taken in connection with the accompanying drawing, in which.

DESCRIPTION OF THE PREFERRED EMBODIMENT

Figure 1:
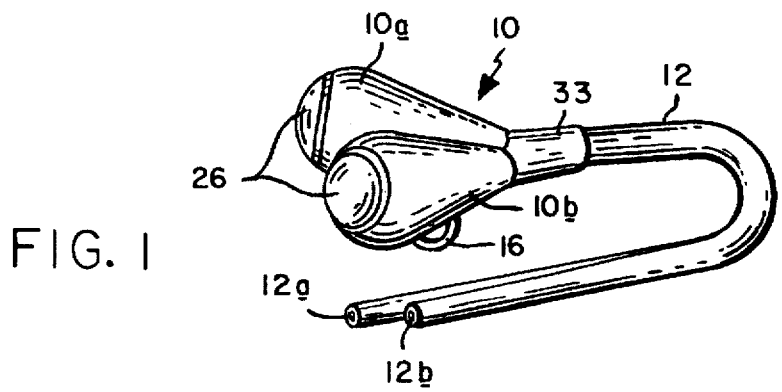
FIG. 1 is an isometric view of a vascular access device incorporating the invention.

Referring to FIG. 1 of the drawing, the subject access port for hemodialysis comprises a dual chamber head 10 connected to a flexible dual-lumen outlet catheter 12. Preferably, the distal end of the catheter is designed so that the exit points of the catheter's lumens 12a and 12b are spaced apart from one another by about 1 inch. This helps to reduce unwanted recirculation, i.e., dialyzed blood returning to the patient via one lumen being drawn back immediately into the other lumen.

Figure 2:
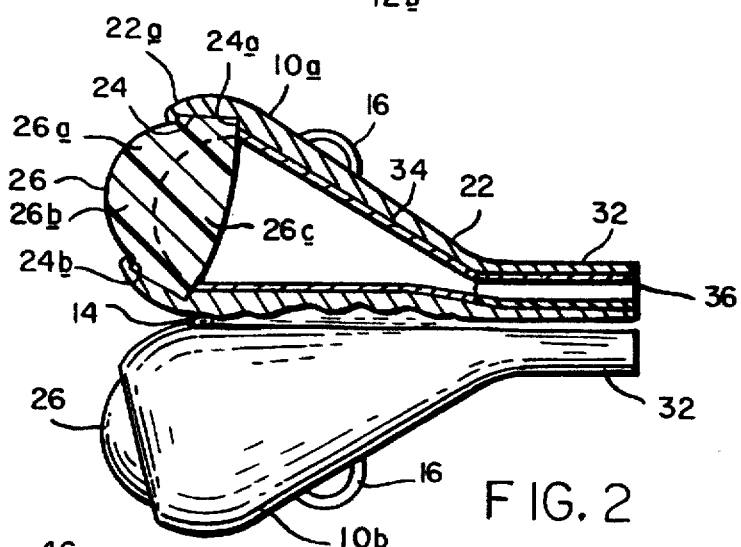
FIG. 2 is a plan view on a larger scale, with parts broken away, of the head portion of the FIG. 1 device.

As best seen in FIGS. 1 and 2, head 10 comprises a pair of mirror-image conical ports 10a and 10b joined together at a common line of tangency by a weld line 14. Suture rings 16 are present at the opposite sides of head 10 so that when the head is implanted into the body, it can be sutured to adjacent tissue to anchor the head.

Typically, head 10 is positioned in the patient just below the clavicle while the distal end of catheter 12 is placed in the superior vena cava.

Referring to FIG. 2, the ports 10a and 10b each comprise a conical shell 22 whose larger end has a rounded exterior surface 22a. A conical groove 24 is inscribed in the interior surface of the shell adjacent to that larger end for seating a needle-penetrable self-sealing septum 26. Septum 26 is "shoe-horned" into the open end of shell 22 so that its inner edge seats on the inner wall 24a of groove 24 and so that the outer edge 24b of that groove overhangs the septum, thereby retaining it in place. Septum 26 has a rounded raised central portion or dome 26a which protrudes from the end of the shell. When the head 10 is implanted in the body, that raised portion 26a can be felt under the skin so that a needle can be aimed properly at the septum.

While not essential, the illustrated septum 26 is actually composed of two layers 26b and 26c of different durometer materials. The upper or outer layer 26b is of a relatively high durometer material such as 70 SHORE A blend silicone for strength to avoid blowout. On the other hand, the lower or inner layer 26c is of a lower durometer material, e.g., 20 SHORE A silicon rubber, which can maintain a seal despite many needle punctures.

Still referring to FIG. 2, a small integral outlet tube 32 leads from the smaller end of each shell 22. Preferably, the outlet tubes 32, which form the apexes of the conical shells 22, do not lie along the axes of the shells. Rather, they curve away from the cone axes so that the distal end segments of the tubes form an angle with the axes of the respective conical shells. This configuration allows the two shells 22 to be joined at the weld line 14, with the distal ends of the outlet tubes being parallel to the line of tangency and spaced apart a distance equal to the spacing of the catheter lumens 12a and 12b.

The proximal end of the dual lumen catheter 12 are engaged over the two outlet tubes 32 and a sleeve 33 (FIG. 1) may encircle that catheter end to provide stress relief at that location.

Conical ports 10a and 10b, with the features described, may be manufactured relatively easily by machining a radially symmetric conical shell 22 with a straight outlet tube 32 whose axis is coincident with the axis of the conical shell and then bending the outlet tube the desired amount, e.g., 20°. Ports manufactured in this manner maintain smoothly converging flow passages free of sharp corners and abrupt changes in diameter. The material of the shells 22 should have the desired ductility and acceptable biocompatability for long term implantation in contact with blood. We have found that commercially pure titanium ASTM B348 grade 1 or 2 is a suitable material.

The surface properties and surface finish of the blood contacting parts of the device 10 have an important effect on the performance of the device. It is desirable to have the blood contacting surfaces as smooth as possible in order to prevent thrombus formation and damage to the blood cells. Highly polished internal surfaces can be produced inside each shell 22 and each outlet tube 32 by pumping a slurry of abrasive material through the shells. Slurries of increasingly finer grits may be used until the desired interior surface finish is obtained.

The blood compatibility of device 10 can be improved further by employing materials with inherent thromboresistance. One such material is carbon of the type used in the construction of artificial heart valves. The superior blood contacting performance of carbon has been attributed to its ability to adsorb onto its surface a limited amount of albumin and fibrinogen from the blood. This protein adsorption results in a lowering of the surface energy of the carbon and the generation of a non-clotting surface.

Carbon can be placed on the internal surfaces of each shell 22 and each outlet tube 32 by a vapor deposition process, rendering the coated surface more thromboresistant than a bare titanium surface. However, such a coating is quite thin and may not be suitable for those surfaces of the device which are likely to be contacted by the sharp tip of an hypodermic needle during normal use of the device. In other words, the access needle may scrape off some of the thin carbon coating. For those surfaces, pyrolitic carbon may be used because that material, as well as being thromboresistant, is harder than the needle material.

One drawback to using pyrolitic carbon is that it is difficult and expensive to fabricate pyrolitic carbon components with complicated shapes. However, the present device 10 composed of the conical shells 22 allows use of self-supporting pyrolitic carbon inserts or liners of simple conical geometry. A liner such as this is shown at 34 in FIG. 2. The liner 34 creates a thromboresistant, as well as a scratch resistant, surface over most parts of the shell's interior. There is no need to bond the carbon liner 34 to the shell 22 since it is mechanically captured by the internal geometry of the shell and the septum 26. The remaining interior surface of titanium, e.g., at outlet tube 32, can be provided with a carbon coating 36 by a standard deposition process because it will never be contacted by an access needle. The above-described abrasive slurry procedure may then be practiced on the composite port body in order to ensure that the transition between the carbon liner 34 and the interior coating 36 is a smooth one.

Figure 3A:
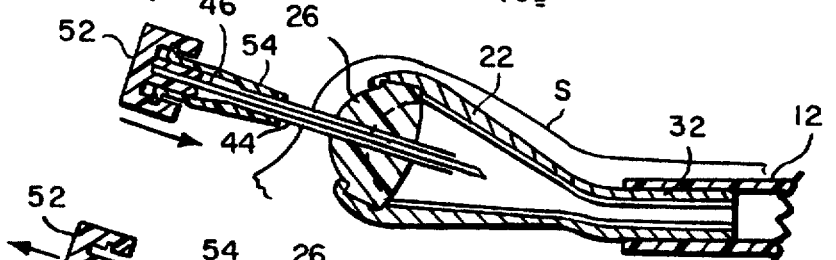
FIGS. 3A to 3C are diagrammatic views illustrating the use of the FIG. 1 device.
Figure 3B:
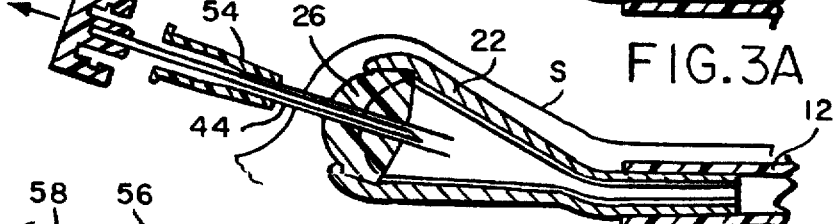
Figure 3C:
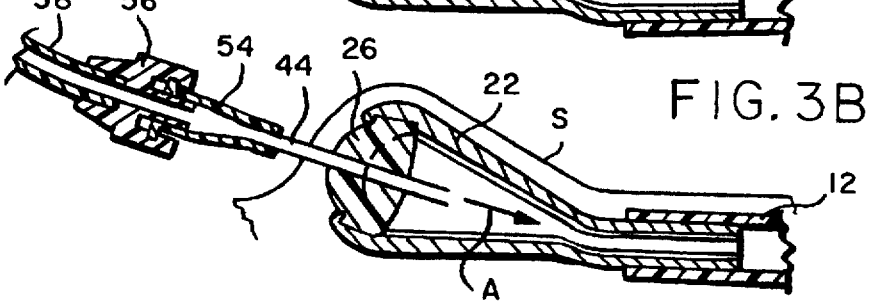

In use, the device 10 may be implanted under the skin S of the chest wall just below the clavicle as shown in FIGS. 3A to 3C. The distal end or tip of catheter 12 is normally placed in the junction of the superior vena cava in the right atrium of the heart. For the tip to reach that location, the catheter is routed through a smaller vessel which joins the vena cava, such as the internal or external jugular vein. The subclavien vein can also be used, but is generally held in reserve if there is a chance that it will be used to construct an access fistula for the patient at some future date.

When the patient is to be dialyzed, the flow path in each port 10a, 10b is accessed by a special hypodermic needle shown generally at 42. Needle 42 includes a relatively large diameter cannula 44, e.g., 12 to 16 gage, having a stylet or obturator 46 which occludes the lumen of the cannula when the needle is inserted through septum 26 into port 10a or 10b. With the stylet in place, the needle cannula may penetrate the septum 26 as shown in FIG. 3A without coring the septum. Resultantly, there is minimal fluid turbulence and thrombus formation. Yet, because of the bend in outlet tube 32, the cannula cannot be inserted into tube 32 far enough to contact, and possibly damage, outlet catheter 12.

Preferably the stylet 46 is provided with an hub 52 at its proximal end which releasably engages to a connector or hub 54 at the proximal end of the cannula. Once needle 42 is inserted into the port 10a or 10b, the hub 52 is decoupled from connector 54 and the stylet 46 is withdrawn from the cannula 44 as illustrated in FIG. 3B. Finally, connector 54 is coupled to a mating connector 56 attached to the end of a tube 58 connected to the dialysis machine as shown in FIG. 3C. When inserted, cannula 44 is in a direct line with the entrance end of outlet tube 32 and the gradually converging walls of liner 34. Therefore, fluid flows directly from the cannula to that tube as shown by arrows A in FIG. 3C.

When the treatment is completed, both flow paths of the device 10 are flushed and "locked" with heparinized saline, the cannulas 44 are removed and sterile dressings are applied over the puncture sites in skin S. Since the entire catheter 12 as well as the ports 10a and 10b are totally implanted and thereby occupy a water-filled environment, liquid contained in the catheter lumens 12a and 12b is not lost by diffusion through the catheter walls. Accordingly, the heparinized saline "lock" is maintained much longer than is the case with those catheters which do penetrate the skin. This improved retention of the heparin lock results in fewer incidents of the catheter becoming occluded with thrombus.

When the patient is not undergoing dialysis, his or her activities are not restricted appreciably by the presence of the device 10 in the body. The patient is still free to swim or bath as he or she pleases. Furthermore, there is no requirement to change dressings at a catheter exit site as there would be with conventional transcutaneous hemodialysis catheters.

The present port may also serve as a route to administer IV medication or to obtain blood samples. In these instances, smaller gage, non-coring or Huber tip needles commonly used with chemotherapy ports may be used to access the device 10.

It will thus be seen that the objects set forth above, among those apparent from the preceding description, are efficiently attained and, since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention described herein.

What is claimed is:

1. A vascular access device for hemodialysis, comprising:

a pair of similar, generally conical, hollow shells, each shell having an entrance end and a smaller exit end defining a smoothly converging flow passage therebetween, and an axis extending between said ends;

means for connecting said pair of shells together along a common line of tangency, each of said shells being disposed with said axis at an acute angle relative to said common line of tangency;

a pair of self-sealing septa closing said entrance ends of said pair of shells; and a pair of outlet tubes having corresponding first ends respectively extending from said exit ends of said pair of shells, said first ends of said pair of outlet tubes being spaced apart and disposed parallel to said line of tangency, such that when blood flows through each of said shells it follows said smoothly converging flow passage along said axis between said entrance end and said exit end of said shell, and undergoes a change in direction equal to said acute angle as it passes into said respective outlet tube.

2. The device defined in claim 1 wherein said pair of septa are domed and protrude from their respective shell entrance ends.

3. The device defined in claim 1 and further including a pair of external suture rings mounted to said pair of shells.

4. The device defined in claim 1 wherein said pair of shells are of titanium, and said pair of septa are of silicone rubber.

5. The device defined in claim 1 and further including a flexible, dual-lumen catheter having one end attached to said opposite ends of said pair of outlet tubes so that the outlet tubes communicate with different lumens of the catheter.

6. The device defined in claim 1 and further including thromboresistant covers covering the internal surfaces of said pair of shells and said pair of outlet tubes.

7. The device defined in claim 6 wherein said covers are composed of carbon.

8. The device defined in claim 6 wherein the thromboresistant covers covering the internal surfaces of said pair of shells comprise conical self-supporting liners which conform to the internal shapes of said shells and fit snugly between the septa and outlet tubes of the respective shells.

9. The device defined in claim 8 wherein said liners are of pyrolitic carbon.

10. The device defined in claim 1 and further including a needle for accessing said device by piercing at least one of said pair of septa, said needle including a cannula having a lumen;

a connector affixed to one end of the cannula;

a stylet sized to be received in and extend the entire length of said lumen, and a stylet hub affixed to one end of the stylet, said hub and said connector including coacting coupling means for releasably securing said hub and said connector together when the stylet is received in the cannula lumen.

11. The device defined in claim 10 wherein the cannula is a 12 to 16 gage cannula.

12. The device defined in claim 1 wherein said pair of septa are each composed of a first layer of relatively high durometer resilient material and a second parallel layer of relatively low durometer resilient material.

13. The device defined in claim 11 wherein said layer of low durometer material is located inside the corresponding shell.

14. A vascular access device for hemodialysis comprising a pair of similar generally conical hollow shells each shell having an entrance end and a smaller exit end;

means for connecting the pair of shells together;

a pair of self-sealing septa closing the entrance ends of said pair of shells;

a pair of outlet tubes having corresponding first ends extending from the exit ends of said pair of shells, and thromboresistant covers covering the internal surfaces of said pair of shells and said pair of outlet tubes.

15. The device defined in claim 14 wherein the thromboresistant covers covering the internal surfaces of said pair of shells comprise conical self-supporting liners which conform to the internal shapes of said shells and fit snugly between the septa and outlet tubes of the respective shells.

16. A vascular device, comprising:

a pair of similar generally conical, hollow shells, each shell having an entrance end and a smaller exit end defining a smoothly converging flow passage therebetween, and an axis extending between said entrance end and said exit end;

means for connecting said pair of shells together along a common line of tangency, each of said shells being disposed with said axis at an acute angle relative to said common line of tangency;

each shell having a self-sealing septum closing said shell entrance, said septum being composed of at least two layers of different durometer rubber-like materials; and a pair of outlet tubes having corresponding first ends respectively extending from said exit ends of said pair of shells said first ends of said pair of outlet tubes being spaced apart and disposed parallel to said line of tangency, such that when blood flows through each of said shells it follows said smoothly converging flow passage along said axis between said entrance end and said exit end of said shell, and undergoes a change in direction equal to said acute angle as it passes into said respective outlet tube.

17. The device defined in claim 14 wherein the thromboresistant covers are composed or carbon material.

18. The device defined in claim 17 wherein said carbon material is pyrolitic carbon.

19. The device defined in claim 16 wherein said layer of low durometer material is located within the shell.

* * * * *